United States Patent [19]

Mikesell

[11] 4,098,132
[45] Jul. 4, 1978

[54] ULTRASONIC SEARCH WHEEL PROBE

[75] Inventor: Charles R. Mikesell, Idaho Falls, Id.

[73] Assignee: The United States of America as represented by the United States Department of Energy, Washington, D.C.

[21] Appl. No.: 825,502

[22] Filed: Aug. 17, 1977

[51] Int. Cl.² ............................................ G01N 29/04
[52] U.S. Cl. ...................................................... 73/639
[58] Field of Search .................. 73/632, 639, 642, 644

[56] References Cited

U.S. PATENT DOCUMENTS

| 3,257,843 | 6/1966 | Cowan | 73/639 |
| 3,423,993 | 1/1969 | Lynnworth | 73/639 |
| 3,832,889 | 9/1974 | Bauer | 73/642 |

FOREIGN PATENT DOCUMENTS

| 1,294,404 | 10/1972 | United Kingdom | 73/639 |
| 224,935 | 8/1968 | U.S.S.R. | 73/644 |

Primary Examiner—Richard C. Queisser
Assistant Examiner—John P. Beauchamp
Attorney, Agent, or Firm—Dean E. Carlson; Frank H. Jackson; Paul A. Gottlieb

[57] ABSTRACT

A device is provided for reducing internal reflections from the tire of an ultrasonic search wheel probe or from within the material being examined. The device includes a liner with an anechoic chamber within which is an ultrasonic transducer. The liner is positioned within the wheel and includes an aperture through which the ultrasonic sound from the transducer is directed.

11 Claims, 4 Drawing Figures

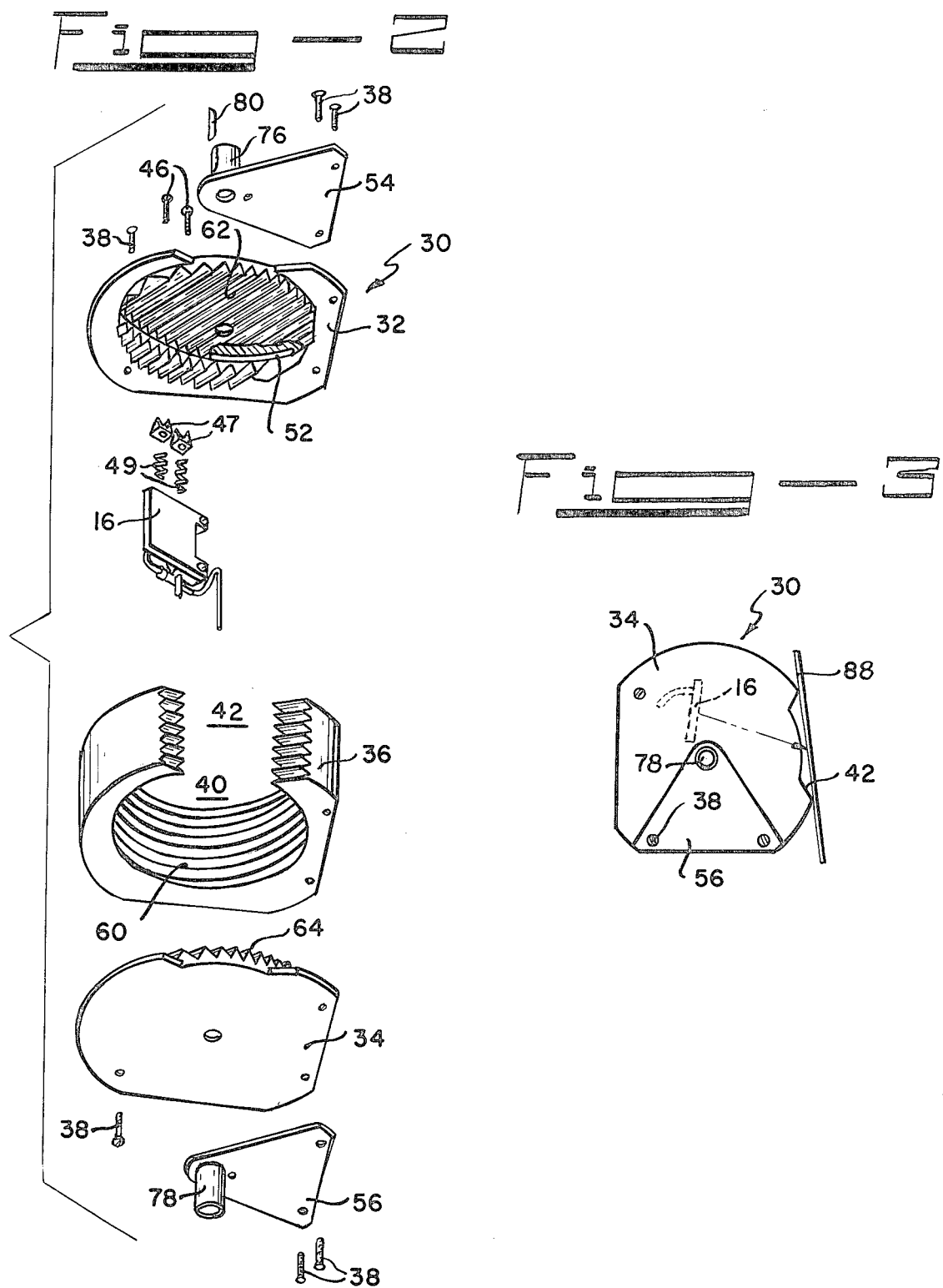

ULTRASONIC SEARCH WHEEL PROBE

CONTRACTUAL ORIGIN OR THE INVENTION

The invention described herein was made in the course of, or under, a contract with the UNITED STATES ENERGY RESEARCH AND DEVELOPMENT ADMINISTRATION.

BACKGROUND OF THE INVENTION

Presently used techniques for examination of metals by ultrasonic methods require coupling high frequency (1-5 MHz) energy of a transducer to the material being examined, while maintaining a selected angle of incidence for the ultrasonic beam with respect to the material surface. One method of doing this is by use of an ultrasonic search wheel probe. The search wheel probe consists of a fixed position axle assembly, transducer and thin membrane balloon tire filled with a liquid to couple the sound to the material.

During ultransonic tests using a search wheel, the transducer within the wheel is positioned at a predetermined angle to the material surface, and the wheel is placed in fixed relation on the part being examined, which is wetted to provide coupling. The transducer generates an ultransonic beam and this beam travels from the transducer to the inside of the tire, where both reflection and refraction occur. The refracted beam subsequently enters the part, where defects are detected by monitoring the reflections of this beam. The beam reflected at the inside diameter of the tire may bounce, reflect and refract several times internally in the tire and be interconverted among several sonic modes. The beam entering the material may also encounter similar effects as a result of the material's structure and configuration. Reflections of this beam received during the time interval required for examination of the part may be confused and misinterpreted as defects by the analysis devices.

It is therefore an object of this invention to provide an improved search wheel probe.

Another object of this invention is to provide an improved search wheel probe with limited undesirable reflections of the ultrasonic beam both internal and external to the search wheel.

SUMMARY OF THE INVENTION

An ultrasonic search wheel having an ultrasonic transducer and a balloon tire filled with a fluid is provided with a liner. The liner defines a chamber within which the transducer is positioned. The liner itself is within the tire which is filled with the coupling fluid. The walls of the chamber of the liner which generally surround the transducer are serrated in a configuration that redirects, dampens, or cancels undesirable reflected acoustic beams. In one embodiment, the liner is provided with an aperture out which the desired ultrasonic beam may be directed towards the part surface being tested. The aperture limits return of off-angle reflections to the transducer. In another embodiment, the liner includes a collimator out of which the beam is directed. The chamber is provided with means for varying the angle of the transducer with respect to the part.

BRIEF DESCRIPTION OF THE DRAWINGS

FIG. 2 is a blowup of the liner of FIG. 1;

FIG. 3 shows the liner as used during ultrasonic tests; and

DETAILED DESCRIPTION OF THE PREFERRED EMBODIMENT

Figure 1:
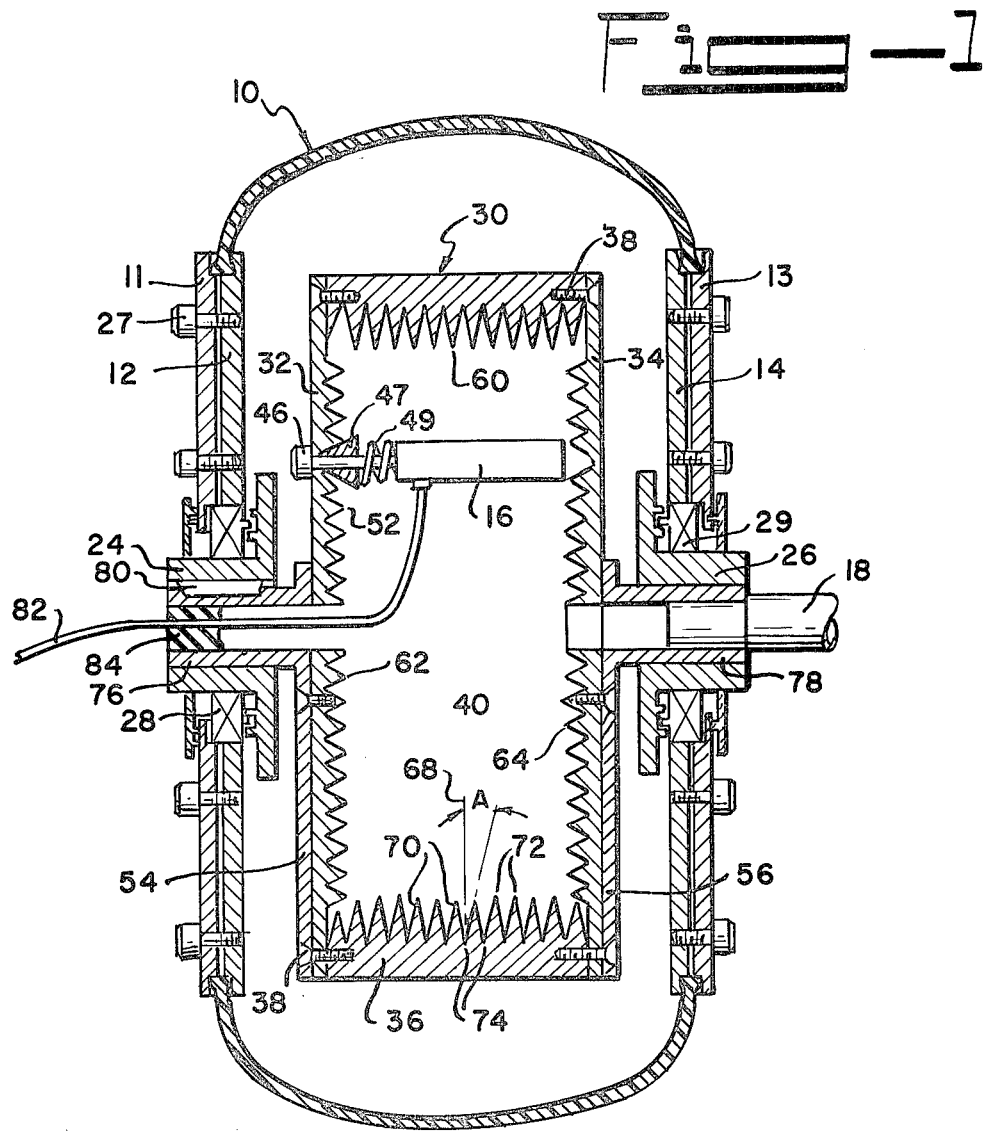
FIG. 1 is a cross section of a search wheel having an internal liner.

Referring to FIG. 1 there is shown an ultrasonic search wheel probe. The search wheel probe includes an outer tire 10 and clamping rings 11, 12, 13 and 14. Within the area defined by the tire 10 and rings 12 and 14 is positioned a transducer 16. The tire 10 is clamped by rings 11, 12, 13 and 14 with screws 27. The clamping rings are mounted via bearings and pressure seals 28 and 29 on hubs 24 and 26. A coupling fluid is contained within the probe and may be introduced into tire 10 via inlet 18 through hub 26. Sealing bearings 28 and 29 allow tire 10 to rotate about hubs 24 and 26 while the coupling fluid is retained within the assembly. Transducer 16 is maintained in a fixed position within tire 10, as will be described. The hubs 24 and 26 are rigidly coupled to a yoke (not shown) to control positioning of the probe. Inspection of a piece is made by using the yoke to move the tire along the piece, with the hubs fixed and the transducer maintained fixed at a predetermined angle with respect to the piece. The transducer transmits and then receives an ultrasonic signal and from this procedure information is obtained about the piece being examined. Problems arise due to the unwanted, internal reflections of the transmitted signal caused by tire 10 and unwanted reflections from the piece. To reduce the unwanted reflections a liner 30 is provided which is positioned within the probe and within which is mounted transducer 16.

Referring to FIG. 2 there is shown the liner 30 exploded. In this embodiment, the liner is comprised of two sides 32 and 34 and a cylindrical main body 36. Sides 32 and 34 are attached to main body 36 with screws 38 forming an enclosed chamber 40. Main body 36 is not fully closed with an opening 42. With the chamber 30 fully assembled the opening 42 serves as an aperture through which ultrasound may be directed to the workpiece. Transducer 16 is mounted within liner 30 via screws 46, springs 49 and wedge blades 47 for rigidly coupling transducer 16 to side 32. Side 32 is provided with an angled slot 52 through which the coupling of the transducer is facilitated. Transducer 16 can be mounted anywhere along slot 52 to provide a means for varying the transducer position with respect to the piece to be inspected. Attachment plates 54 and 56 are provided to facilitate mounting of the entire assembly within the probe.

Liner 30 defines chamber 40. The walls 60, 62 and 64 of chamber 40 are designed to minimize reflections therefrom by absorbing, dissipating and/or scattering ultrasonic energy travelling along undesired paths and preventing such energy from reaching transducer 16. The walls 60, 62 and 64 are serrated. Wall 60 of main body 36 which forms the circumferential surface of cylindrical chamber 40 is serrated circumferentially. Walls 62 and 64 of sides 32 and 34, respectively, are serrated in a linear direction. The serrations on side walls 62 and 64 are generally aligned with the beam to be transmitted from transducer 16. Thus in FIG. 1, the aperture is cut away and would lie facing out of the drawing so the profile of the serrations is seen. The serrations reduce the adverse sound reflections by (1) destructive interference when the point to point serration spacing approximates ½ wavelength of the center sound frequency, (2) redirection of the sound into the serration groove when the included angle of the groove is less than 60°, and (3) transmission of beam energy into the chamber material because of close impedance matching of the material to the fluid. For best results therefore the serrations should be spaced approximately ½ wavelength of the center frequency of the sound beam giving significant cancellation rather than reflection at the liquid-to-chamber 40 inside surface. The angle A of the cut of the serrations, i.e. the angle each serration side 70 makes with a line 68 normal to the unserrated surface of chamber 40 should be no greater than 20° to ensure that reflected sound is driven deeper into each groove defined by serrated side 70 and thereby be dissipated. Ideally, angle A should approach 0°. Tip 72 of serrations and groove roots 74 should be sharpened to minimize their reflectivity. Maximum radii of approximately 0.004 inches for roots 74 and tip 72 are desirable.

The material for liner 30 is selected for its acoustic absorption and impedance matching characteristics with respect to the fluid within tire 10. Acetal resin is an example of an acceptable material. The size of the chamber should be such that tire 10 is capable of having a proper foot print when the probe is pressed against the object to be tested. The proper foot print is one which will flatten on the part over an area which covers the area of the incident beam of energy from transducer 16.

The liner 30 is positioned within the probe assembly as shown in FIG. 1 by insertion of the extending portions 76 and 78 of each plate 54 and 56 into hubs 24 and 26. The entire assembly of liner 30 is held rigid with respect to hubs 24 and 26 by antirotation key 80 which fits into a slot in portion 76 of plate 54. Electrical connection to transducer 16 for controlling operation of transducer 16 and transmitting the returning reflected information to associated instrumentation is provided via lead 82 which exits the probe via seal 84.

Referring to FIG. 3 there is a shown a liner 30 without the tire assembly to illustrate the operation of the chamber 40. Transducer 16 is positioned in slot 52 to achieve the desired incident beam angle with respect to part surface 88. Slot 52 is generated about a point on surface 88, permitting the beam to pass through aperture 42 regardless of the incident angle. Aperture 42 controls the size and shape of the transmitted beam and prevents externally generated off angle reflected beams from entering the liner.

Figure 4:
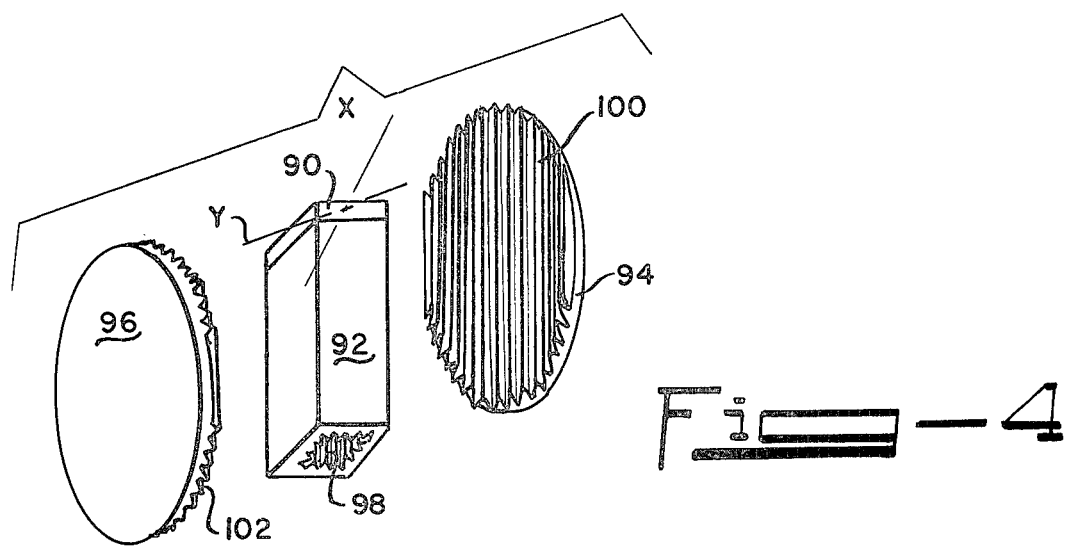
FIG. 4 shows an alternate embodiment of the liner.

In the embodiment shown in FIG. 1, transducer 16 had only one freedom of movement, i.e. it could be moved radially with respect to aperture 42 in slot 52. New generations of search wheel probes are provided with an additional freedom of movement in that the transducer's position can be varied axially as well as radially. A liner adapted for use with such a probe is shown in FIG. 4. Here transducer 90 is provided with means (not shown) to allow its movement in the radial direction about the y axis and in the axial direction about the x axis. The main body portion of the liner of FIG. 1 is replaced with a collimator 92 which moves with transducer 90 and surrounds the desired beam path. The actual dimensions and shape of the cross section of collimator 92 are a matter of design choice. In FIG. 4 the cross section shown is square. For example, a circular cross section could be utilized. The cross section of the collimator 92 should be no bigger than the beam transmitting area of transducer 90. Side walls 94 and 96 of the liner are stationary with respect to the part being examined. The inside walls 98 of collimator 92 and the inside walls 100 and 102 of side walls 94 and 96 are serrated as described previously. The serrations are all linear and in a direction generally parallel to the beam path. The opening in collimator 92 serves as the aperture for the developed beam.

Significant features of the design which will reduce the internal reflection are the selection of a low acoustical impedance material for liner 30 to reduce the surface reflectivity, coverage of the entire internal liner surface with acoustic damping material, selection of serration spacing to approximate the ½ wavelength of the center frequency sound, elimination of reflecting surfaces normal to the liner surface by the serration and maintaining sharp tips and groove roots, maintaining the angle of the serrated surface so that a beam normal to the surface would be reflected into rather than out of the groove, and use of an aperture to define beam size, shape and reflected beam acceptance angle.

The embodiments of the invention in which an exclusive property or privilege is claimed as follows:

1. In an ultrasonic search wheel probe having an ultrasonic transducer positioned inside a balloon tire filled with a fluid, the tire and fluid coupling the sound from the transducer to an object being examined, the improvement in the probe for reducing undesirable reflections comprising:
   a liner whose inner walls are serrated and within which is positioned the transducer, said liner being mounted in said probe inside the wheel, said liner having an aperture through which said transducer is capable of directing ultrasound and receiving ultrasound.

2. The device of claim 1 wherein said liner includes a cylindrical chamber with said transducer beam aligned radially with said cylindrical chamber.

3. The device of claim 2 wherein said aperture extends through said liner into said chamber through a portion of the circumferential surface of said cylindrical chamber.

4. The device of claim 3 wherein the serrations in the circumferential surface of said cylindrical chamber are aligned circumferentially with respect to said cylindrical chamber.

5. The device of claim 4 wherein the serrations in each side of said cylindrical chamber are linear and parallel and generally aligned with a beam directed from the transducer through said aperture.

6. The device of claim 5 wherein the portion of said liner forming one side of said chamber is provided with a slot, the transducer being coupled to said liner through said slot and with the angle of exit of a beam transmitted by the transducer through said aperture depending upon the position along said slot at which the transducer is coupled to said liner.

7. The device of claim 5 wherein the mounting of said liner and the transducer coupled thereto within said probe is rigid so that the tire is free to rotate while said liner and the transducer are fixedly maintained at a predetermined alignment.

8. The device of claim 1 wherein said liner includes fixed opposing side walls between which said transducer is positioned, and a collimator positioned between said side walls through which ultrasound is directed and received by said transducer.

9. The device of claim 8 wherein the surfaces of said side walls facing each other and the interior surface of said collimator are serrated with said serrations being linear and aligned generally parallel to the direction of any beam directed by said transducer through said collimator.

10. The device of claim 1 wherein said serrations are spaced apart approximately ½ wavelength of the center frequency of a particular beam generated by the transducer.

11. The device of claim 10 wherein the angle A each side of said serrations makes with a normal thereto is no more than 22.5°.

* * * * *